United States Patent [19]

Wang

[11] 4,239,966

[45] Dec. 16, 1980

[54] DETECTION OF ATOMS USING MONOCHROMATIC X-RAYS

[76] Inventor: Chia G. Wang, P.O. Box 211, Millwood, N.Y. 10546

[21] Appl. No.: 70,586

[22] Filed: Aug. 29, 1979

[51] Int. Cl.³ .............................................. G01N 23/20
[52] U.S. Cl. ..................................... 250/275; 250/444
[58] Field of Search .............. 250/273, 274, 275, 320, 250/323, 526, 305, 306, 307, 444

[56] References Cited

U.S. PATENT DOCUMENTS

| 3,735,128 | 5/1973 | Palmberg | 250/305 |
| 3,919,548 | 11/1975 | Porter | 250/272 |
| 4,158,770 | 6/1979 | Davis et al. | 250/273 |

Primary Examiner—Alfred E. Smith
Assistant Examiner—T. N. Grigsby
Attorney, Agent, or Firm—Ladas & Parry

[57] ABSTRACT

A method and apparatus for detecting, in a specimen, atoms, of an element having an atomic number of at least 20, comprising irradiating the specimen with monochromatic X-rays having a wavelength capable of inducing an inner shell ionization of the atoms with subsequent auger cascade and recording the emission of the auger electrons emitted by the cascade on a photographic emulsion, the monochromatic X-rays being produced by exposing a secondary radiator to X-rays to produce consequent secondary radiation in the form of the monochromatic X-rays.

11 Claims, 1 Drawing Figure

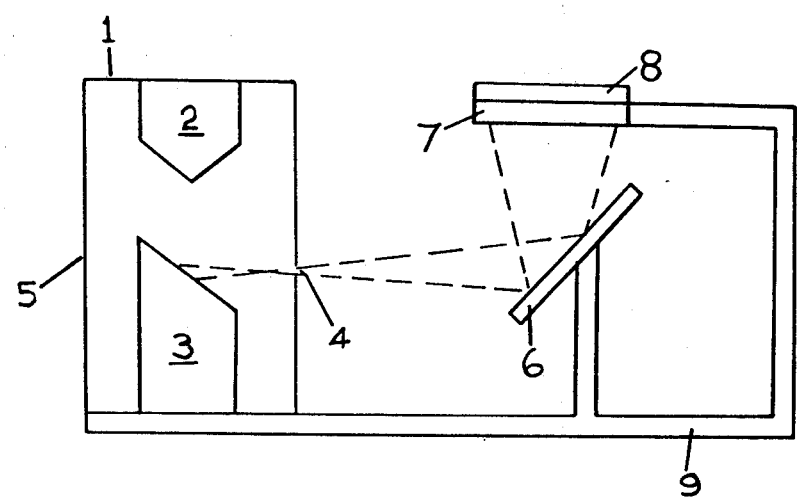

DETECTION OF ATOMS USING MONOCHROMATIC X-RAYS

This invention relates to the detection of atoms of a desired element in a specimen and particularly, although not exclusively, to the detection of iodine atoms or bromine atoms in a biological specimen.

It is known that the irradiation of elements having an atomic number of 20 or more by monochromatic X-rays on the K-edge of the atoms of the element will produce an inner shell ionization leading to an auger cascade ejecting electrons from the atom. It is also known that electrons ejected by an atom are recordable on a photographic film grain. In the case of iodine (I) as many as 18 auger electrons may be created from an inner shell ionization while in the case of bromine (Br) as many as 13 auger electrons may be created. In the present invention it is proposed to utilise this phenomena to detect the quantity and distribution of atoms of an element present in a specimen, for example a biological specimen.

DNA genomes in the cell structure of a biological specimen are not usually visible under a light microscope, but become visible when stained with cerain basic dyes. When the genome is metabolically active, it extends over a relatively larger region, can only be stained lightly and shows considerable variation of shade. When inactive, the DNA strands which are tightly twisted and folded together can be stained deeply and show sharply demarcated lumps or granules. Much genetic information has been learned from the morphology of chromatids which can be clearly examined during the metaphase of mitosis where the mitotic process was stopped with colchicine and the cells squashed and stained. Similarly, the use of certain fluorescent dyes to intercalate between pairs of DNA bases, and use the lumination of the dye under ultraviolet light or X-ray, provides a clear outline of the chromosome. In order to learn the metabolic functions on a molecular level, labelled molecules, such as the $^3$H-thymidine is often used in autoradiography. Electrons, emitting from the tritium decay, can be recorded in a photographic emulsion. But the dosage of the radioactivity is such that it must not interfere with the metabolic processes, and the radioactive decay time of tritium at a half-life of 12 years is often too inconveniently long. A more recent tool is the use of restrictive enzymes to cut the genome at some designated sections. The use of these methods, and of some combinations of them, have provided genetic research with powerful tools.

According to the present invention there is provided a method of detecting, in a specimen, atoms, of an element having an atomic number of at least 20, comprising irradiating the specimen with monochromatic X-rays having a wavelength to induce an inner shell ionization of said atoms with subsequent auger cascade, and detecting the auger electrons emitted by the cascade.

According to the invention there is also provided an apparatus for detecting, in a specimen, atoms of an element having an atomic number of at least 20, comprising a source of monochromatic X-rays having a wavelength to induce an inner shell ionization of said atoms with subsequent auger cascade, and means for detecting the auger electrons emitted by the cascade.

In both the method and apparatus forms of the present invention the detection means is, in a preferred form of the invention, a photographic emulsion which includes substantially no atoms of the element the detection of which is desired.

Also in a preferred form of the invention the source of monochromatic X-rays of the desired wavelength is a secondary radiator including an element, which is excited by X-rays from an X-ray generator to produce excitation of the element and consequent secondary radiation in the form of X-rays of the desired wavelength.

The method and apparatus of the present invention is particularly useful for ascertaining the quantity and distribution of atoms of an element which have been added to a biological sample as a "label." In a particular application the atoms of the element to be detected are used to "label" a DNA molecule or certain proteins or enzymes, with a element being non-radioactive (cold) under metabolic conditions, for example, bromine or iodine. As the elements concerned are virtually non toxic, relatively large amounts can be administered for irradiation by a monochromatic X-ray on the K-edge of the element to be detected to produce inner shell ionization. Upon the occurrence of the ionization electrons in the outer shells fall in, with certain probability, to fill the inner hole. The difference of potential energy between different shells that the in falling electron switches, may or may not lead to a radiative transfer. An auger cascade is a sequence of non-radiative transfer from a single inner hole in which an outer shell electron falls in to fill the hole and due to its difference in potential energy ejects a neighbouring electron, creating two holes in the process. Following this more outer shell electrons fall in to fill the holes and their difference in potential energy results in the ejection of still more electrons from the atom. As many as 18 auger electrons may be created from an iodine inner shell ionization and as many as 13 from bromine.

The auger electrons are mostly of low energy and deposit most of their kinetic energy within a very short distance in a biological environment thereby creating extremely concentrated localized multiple ionizations. In contrast, the X-ray which initiates the inner hole is almost transparent to the medium. In the presence of a photographic emulsion, it will record the auger cascade but not the X-ray photons. Due to the fact that auger cascade begins from an inner hole, it is independent of the chemical state of the atomic binding. In the case of bromine, for example, it makes no difference whether the element is contained in BrdU or in AgBr. To detect Br in a specimen, the photographic emulsion must not contain the element Br, similarly, if iodine is the target element, it must not be present in the emulsion. Otherwise, one cannot distinguish whether if the auger electrons originate from the specimen or from the emulsion itself. The choice of the photosensitive material to record the presence of the target element is therefore extremely vital to the method.

A method and apparatus in accordance with the present invention will now be described, by way of example, with reference to the accompanying drawing which is a diagrammatic representation of suitable apparatus.

With reference to the drawing a conventional X-ray tube 1 has a cathode 2 and a target electrode or anode 3 surrounded, except for an X-ray emission window 4, by a shield 5. A secondary radiator 6 is disposed to receive X-rays emitted by the X-ray tube 1 through the window 4 and to emit secondary radiation, induced by these X-rays, in a direction toward a specimen 7 which is coated on the side of the specimen remote from the secondary radiator 6 by a photographic emulsion 8. The X-ray tube, secondary radiator and coated specimen are supported relative to one another by a support structure 9.

When the secondary radiator 6 is exposed to the X-rays emitted through the window 4, the incident radiation is absorbed leading to excitation of the elements characteristic lines as if it were the source, but with a reduced photon density and without the bremsstrahlung. This secondary ignition is a monochromatic X-ray having a wavelength corresponding to the elements characteristic lines and is emitted by the secondary radiator 6 toward the specimen 7. These monochromatic X-rays, which are on the K-edge are absorbed by the element, create an inner shell ionization of the atoms of the element in the specimen thereby initiating an auger cascade with the consequent emission of auger electrons which are mostly of low energy and deposit most of their kinetic energy within a very short distance in the environment of the specimen, for example a biological specimen, thereby creating extremely concentrated localised multiple ionizations. In contrast, the specimen, other than the element concerned, and the photographic emulsion are almost transparent to the monochromatic X-rays with the result that the photographic emulsion will record the auger cascade but not the X-ray photons.

Although the preferred manner of producing monochromatic X-rays of the desired wavelength in the present invention is by the use of the secondary radiator, this is but one of three possible methods which could be used and which are intended to fall within the boundaries of the present invention. A second method is the use of an appropriate anode material plus some filtering, and a third method is the use of a Bragg diffractor.

In a conventional X-ray machine, the potential drop between the anode and the cathode derives directly from the DC rectification of the output of an AC transformer. The sinusoidal line power is first transformed into high voltage, retaining the AC line frequency, and the simple rectification changes nothing but the negative half-cycles into the positive cycles. As a result, the voltage supplying the X-ray tube changes continuously from zero to $V_{peak}$. For a monochromatic X-ray output where only an optimum of potential drop is required, most part of the potential levels do not produce the desired X-ray photons and is therefore wasted. In order to have a steady monochromatic X-ray output, it is necessary to have a DC power supply with proper current and voltage characteristics.

The second important consideration for the design of a X-ray tube is the target material of the anode. For a typical metal target, it produces a K-edge peak specific to the metal element and a bremsstrahlung tail. If the desired monochromatic X-ray happens to lie within the width of the K-edge peak, a proper choice of the $V_{peak}$ gives a high energy cutoff and the window material of the tube filters away photons of longer wavelength, including the bremsstrahlung tail. Under continuous electron bombardment, the target must dissipate almost all the electron energy (99.8%) in the form of heat. Usually heat dissipates in the form of black-body radiation at high temperature, or is carried away by circulating oil or water. Because of the heat dissipation, most of the target material are metals.

This second method of producing monochromatic X-rays involves some difficulty when the element concerned is bromine or iodine as these materials have high vapor pressure and dissolve easily in water. In order to make the halogen material suitable for use as a target to sustain the electron bombardment, some special housing is required to contain them.

The third method of producing a monochromatic X-ray is the use of a crystal diffractor. The Bragg diffraction gives a condition:

$$2d \sin \theta = n\lambda$$

that from a point source to a point target T, at a given diffraction angle $\theta$ and the crystal spacing d, only photons with wavelength $\lambda$ satisfying the Bragg condition can be coherently reflected. Most of the photons diffracted are at the first harmonic $n=1$. The diffractor is usually curved in order to focus the monochromatic photons onto the target material. There are now commercially available diffractors with the proper spacing d to cover each element of the K-edge radiation for any element with $Z \geq 10$. However, a suitable diffractor is expensive and places severe limits on the application, such as requiring a small dimension of specimen and as a result of the low photon number density of the output.

Accordingly the secondary radiator method of producing monochromatic X-rays of the desired wavelength is the preferred method for use in the present invention.

The use of X-ray photons in accordance with the present invention to do chemical element analysis is to some extent comparable with histochemical analysis. In histological studies, very soft X-rays are used to examine the transmission characteristics of a very thin tissue. In order to obtain the maximum contrast, the preparation of the specimen (thickness, levels of various mineralizations, etc.), the X-ray voltage, choice of the target and the window materials must all be critically compared. In order to avoid the absorption of the soft X-ray photons by air, various vacuum-mount cameras are required for the study. In some contact studies of cytological detail, a resolution as high as 0.2 $\mu$m can be obtained. In the present invention, hard X-ray photons are employed. As these are very penetrating to the specimen as well as the emulsion, and the photographic record is initiated from auger electrons, which give extremely efficient linear-energy-transfer to sensitize the emulsion. With this high contrast the design considerations result in equipment which is relatively simple.

Although not limited to use in the analysis of biological specimens, the present invention is useful in studies of DNA and protein structures in biological specimens with bromine being suitable as a "label" for DNA molecules and iodine being suitable as a "label" for protein.

As will be apparent from the above description the choice of photosensitive material forming the photographic emulsion is important. In the following description the use of target element of iodine or bromine is considered. However, the concepts involved will be seen clearly to apply in situations where the specimen may not be a biological specimen and where the target element is not iodine or bromine.

Photographic images are formed through the deposit of silver. Most negative emulsions are composed mainly of AgBr crystals (grains) suspended in a gelatin and coated with a thin layer of supercoating to prevent sensitization by pressure (handling protection). The supercoating is too thick a layer for low energy electrons to penetrate. Liquid emulsions, such as Kodak NTB2, NTB3 etc., are therefore used to coat directly on the specimen slide for the exposure of $^3$H-thymidine in autoradiography. Emulsions for positive paper composed mainly of AgCl crystals without the supercoating. AgCl crystals are much slower than AgBr crystals. For a typical X-ray film, its response to X-ray irradiation is only 2–7% relative to photons of visible range, and screen-type intensifiers are therefore often used to transform (fluorescence) photons from X-ray to that of visible in order to increase the film's sensitivity. Normal X-ray films also have double coatings, one for fast exposure and another for slow, in order to increase the exposure depth.

The formation of a metallic silver grain requires several steps. A latent image, initiated with as little as only a few silver atoms at a sensitivity speck of the grain, can be caused by photoelectrons or by ionizing charged particles passing nearby. The neutralized silver atoms at the sensitivity speck are stabilized and act as a catalyst to form a development centre attracting additional metallic silver during the process of development. Depending upon the vigor of the development and the accessability of the sensitivity specks to the developer, a latent image speck may or may not be of sufficient size to form a development centre. For transillumination, images block out the illuminating light and dark images are formed whenever there are large deposit of the silver grains. For dark-field illumination, light shines at the images from an oblique angle and each silver grain becomes a source of reflected light and becomes instead the bright area of the image film. The dark-field illumination can reduce the light exposure, retaining the same image resolution. With relatively limited exposure, we shall make use of the dark-field illumination.

For greatly under-exposed images with silver atoms, dark-field illumination can be used with the help of an electronic-image intensifier with the image composed on a television picture tube. Note that with the usual transillumination, when there are too many silver grains, or simply an over-exposure, the image information or resolution is reduced as one cannot distinguish one grain point from another. In dark-field illumination, on the other hand, under-exposure involves smaller number of grains, but the resolution of the the image is not necessarily reduced. With the help of a television lens, the image is recomposed, and in effect, each grain size is amplified to retain the same image quality. With this method, many emulsions of slow exposure speed, such as emulsions composed of AgCl crystals, can become useful. This under-exposure without the loss of resolution is of great importance in many fields of application, for example, medical examinations with X-rays, (e.g. mammography, dental pictures) and in astronomy where the reduction of exposure time can be equated to an increase in telescope size.

While the present invention has been described with particular reference to the detection and recordal of atoms of an element used to "label" a biological specimen, it will be appreciated that the method and apparatus of the present invention is applicable to the detection and recordal of the present of particular elements and the distribution of their atoms in a wide variety of specimens in a wide variety of sciences and technologies (e.g. metallurgy, geology, environmental engineering, polution detection, production and quality control).

It will further be appreciated that while the present invention has been described with respect to a particular method and a particular apparatus, many variations will be apparent to a man skilled in the art upon his becoming aware of the concepts involved in the present invention and that these variations fall within the scope of the present invention as claimed hereinafter.

For example:

A. The secondary radiator may be constructed entirely from the element producing the secondary radiation and this may be of liquid or solid form. When the element is in liquid form the secondary radiator may be in the form of a housing transparent to the X-rays emitted from the X-ray tube and the monochromatic X-rays and which houses the mass of the element to be used to generate the monochromatic X-rays.

B. The specimen may be self supporting or supported on a carrier, for example a glass slide, the material of which will not respond to the monochromatic X-rays to produce any discernible image on the photographic emulsion. These materials will, of course, be readily apparent to those skilled in the art and easily determined by simple experiment.

C. The photographic emulsion may be coated on the specimen itself or on the carrier, between the secondary radiator and the specimen or on the side of the specimen remote from the secondary radiator, between the specimen and the carrier or on the side of the carrier remote from the specimen etc. The critical criteria being that the photographic emulsion be sufficently adjacent the specimen for the recordal of the localised ionisations produced by the auger electrons of the atoms of the element in the specimen which is to be detected.

D. The means for detecting the localised multiple ionisations produced by the auger electrons is not restricted to the use of a photographic emulsion and may involve, for example, a vidicon type or matrix semiconductor type image intensifier and means for displaying or recording these.

The monochromatic X-rays for triggering an auger cascade in bromine have a photon energy of 13.47 KEV and for iodine have a photon energy of 33.17 KEV.

A filter may be used to eliminate wavelengths of X-rays, from the X-ray generator, below the energy of the wavelength of the target element. In this arrangement the specimen and the emulsion and/or the secondary radiator need not be free elements in which an auger cascade is induced by X-rays of a wavelength filtered out by the filter.

I claim:

1. A method of detecting, in a specimen, atoms, of an element having an atomic number of at least 20, comprising irradiating the specimen with monochromatic X-rays having a wavelength to induce an inner shell ionization of said atoms with subsequent auger cascade, and detecting the auger electrons emitted by the cascade, wherein the quantity and distribution of the atoms is recorded on a photographic emulsion which itself includes substantially no atoms of the element, the photographic emulsion being a layer disposed closely adjacent the specimen.

2. A method according to claim 1, including producing the monochromatic X-rays by exposing a secondary radiator having atoms of the element to X-rays thereby to produce excitation of the atoms and consequent secondary radiation in the form of X-rays of said wavelength.

3. A method according to claim 1, wherein the specimen is biological and the element is iodine or bromine.

4. A method according to claim 1, wherein the specimen is a biological specimen in the form of a specimen slide and the photographic emulsion is a liquid emulsion coated directly on the specimen slide.

5. Apparatus according to claim 1, wherein the specimen is a biological specimen slide and the emulsion is a liquid emulsion coated onto the slide.

6. Apparatus for detecting, in a specimen, atoms, of an element having an atomic number of at least 20, comprising a source of monochromatic X-rays having a wavelength to induce an inner shell ionization of said atoms with subsequent auger cascade, and means for detecting the auger electrons emitted by the cascade, wherein the detecting means is a photographic emulsion which includes substantially no atoms of the element, the photographic emulsion being a layer disposed closely adjacent the specimen.

7. Apparatus according to claim 6, including means for relatively positioning the source, specimen and detecting means for the irradiation of the specimen by the monochromatic X-rays and the detection of the resulting auger cascade.

8. Apparatus according to claim 6, wherein the source includes a secondary radiator having atoms of an element arranged for irradiation by X-rays to produce excitation of the atoms and consequent secondary radiation in the form of X-rays of said wavelength.

9. Apparatus according to claim 4, wherein the radiator is a flat plate.

10. Apparatus according to claim 8, wherein the element forming the radiator is a mass of said element captively contained in a container transparent to X-rays.

11. Apparatus according to claim 8, wherein the source includes an X-ray generator.

* * * * *